United States Patent [19]

Plotkin et al.

[11] Patent Number: 5,225,606
[45] Date of Patent: Jul. 6, 1993

[54] ALK-1-ENYL ETHERS

[75] Inventors: Jeffrey S. Plotkin, Monsey, N.Y.; Kolazi S. Narayanan, Palisades Park; Paul D. Taylor, West Milford, both of N.J.

[73] Assignee: Isp Investments Inc., Wilmington, Del.

[21] Appl. No.: 712,766

[22] Filed: Jun. 10, 1991

Related U.S. Application Data

[62] Division of Ser. No. 417,135, Oct. 4, 1989, abandoned.

[51] Int. Cl.$^5$ ............ C07C 43/11; C08B 31/08; C07H 15/04
[52] U.S. Cl. .................... 568/608; 568/45; 568/49; 568/54; 536/111; 536/120
[58] Field of Search .............. 568/68, 45, 49, 54; 536/111, 120

[56] References Cited

U.S. PATENT DOCUMENTS

| | | | |
|---|---|---|---|
| 4,703,114 | 10/1984 | Mori et al. | 568/608 |
| 4,727,199 | 2/1988 | King | 568/620 |
| 4,814,514 | 3/1989 | Yokota et al. | 568/608 |
| 4,960,952 | 10/1990 | Kemp | 568/608 |
| 5,057,627 | 10/1991 | Edwards | 568/618 |
| 5,059,719 | 10/1991 | Edwards | 568/618 |
| 5,110,992 | 5/1992 | Atkins et al. | 568/618 |

FOREIGN PATENT DOCUMENTS

| | | |
|---|---|---|
| 249883 | 12/1962 | Australia . |
| 512875 | 5/1955 | Canada . |
| 300527 | 1/1989 | European Pat. Off. . |
| 6166136 | 12/1981 | Japan . |

*Primary Examiner*—Paul J. Killos
*Attorney, Agent, or Firm*—Marilyn J. Maue; Joshua J. Ward

[57] ABSTRACT

This invention relates to the alk-1-enyl ether reaction product of a hydroxylated compound and an alk-1-enyloxy oxirane containing from 0 to 95% alkyl epoxide.

10 Claims, No Drawings

ALK-1-ENYL ETHERS

This is a division of applicaton Ser. No. 417,135, filed Oct. 4, 1989, abandoned.

In one aspect this invention relates to novel alk-1-enyl ethers which can be employed as radiation or thermally curable molding resins, coatings and adhesives. In another aspect the invention relates to the reaction composition and the process for preparing said alk-1-enyl ethers.

BACKGROUND OF THE INVENTION

Polyallyl ethers derived from polyols and carbohydrates, particularly allylated pentaerythritol, trimethylpropane, and starches and sugars have been widely investigated as monomers suitable for protective coatings. These materials are attractive since they undergo autoxidative polymerization in contact with air. However, because of slow curing rates, color formation and relatively poor substrate bonding strength, films of these allyl ethers have limited commercial use (see ALLYL COMPOUNDS AND THEIR POLYMERS by C. E. Schildknecht, Wiley Interscience, 1973). Additionally many of these monomers and oligomers are thermally unstable and decompose to give off an objectionable odor characteristic of acrolein.

Attempts to prepare high molecular weight monoallyl ethers by free radical or ionic polymerizations have not been successful and result in low molecular weight products in admixture with substantial quantitites of unreacted material which is difficult to separate. According to British Patent 730,670, the polymerization of a allyl glycidyl ether benzene solution in the presence of 3% ditertiary butyl peroxide at 155° C. resulted in a product having a molecular weight of only 500 which was contaminated with a significant quantity of unconverted allyl glycidyl ether. Obviously such materials are unsuitable as protective coatings.

Accordingly, it is an object of the present invention to overcome the above defficiencies and to provide alkenyl derived ethers which are readily polymerizable to thermally stable compounds having superior coating properties and which provide films having good adhesion and high resistance to chemical attack.

Another object of this invention is to provide an economical and commercially feasible process for curing coatings of the present compounds.

Still another object is to provide metal and glass coatings and finishes which are not subject to coloration over extended periods of use.

These and many other objects of the invention will become apparent from the following description and disclosure.

THE INVENTION

In accordance with this invention there is provided a novel, radiation curable, alk-1-enyl ether monomer or oligomer which can be prepared by condensation of an alk-1-enyloxy oxirane containing from 0% to about 95% alkyl epoxide with a mono- or poly- hydroxylated compound. The reaction is illustrated by the following equation:

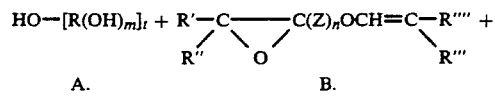
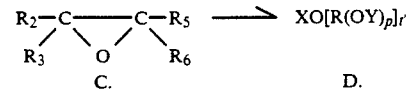

wherein t has a value of from 1 to 50; m has a value of from 0 to 8; when m is a positive integer, R is $C_2$ to $C_{20}$ branched, linear or cyclic alkylene, alkenylene, alkynylene, arylene, aralkylene, alkarylene, aralkenylene or alkenylarylene which radicals are optionally substituted with a carbonyl, vinyl ether, carboxylate, carbonate, alkyleneoxyalkyl, alkenyleneoxyalkyl, halo, hydroxy, alkoxy or a mixture thereof and when m is zero, R can be $C_1$ to $C_{20}$ alkyl, phenyl, benzyl, a polyhydroxylated starch, sugar or cellulose and alkoxylated derivatives of the foregoing or the radical having the formula

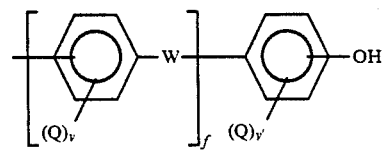

where
W is lower alkyl, sulfur, sulfonyl or oxygen; Q and Q' are each lower alkyl or halogen; v and v' each have a value of from 0 to 4 and f has a value of from 1 to 50;

Z is $C_1$ to $C_8$ alkylene, alkenylene, alkynylene or (alkyleneoxy)$_g$-(lower alkylene) where g has a value of 1 to 8;

R', R'', R''' and R'''' are each independently hydrogen or alkyl having from 1 to 6 carbon atoms;

n has a value of from 1 to 8;

$R_2$, $R_3$, $R_5$ and $R_6$ are each independently hydrogen, $C_1$ to $C_6$ alkyl, alkenyl, or halogenated alkyl or alkenyl;

X is the reacted, ring opened radical of the alkyl epoxide reactant having the formula

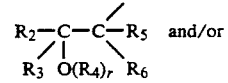

the reacted ring opened radical of the alk-1-enyloxy oxirane reactant having the formula

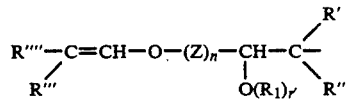

p has a value of from 0 to 8;

t' is the same as t;

each Y is independently hydrogen or a radical designated for X when p has a positive value, and $R_1$ and $R_4$ are each hydrogen or a radical designated for X; when $R_1$ and $R_4$ are X, r and r' each have a value of from 1 to 100 depending upon the stoichiometric ratio of hyroxylated compound with respect to alk-1-enyloxy oxirane or hydroxylated compound with respect to alk-1-enyloxy oxirane and alkyl epoxide reactants, and when $R_1$ and $R_4$ are hydrogen, r and r' have a value of one. Thus, the increasing amounts of total epoxide group in the components of the reaction mixture are reflected in a corresponding progression of ring opened oxide groups substituted in the molecule of the final product.

Accordingly, when the condensation reaction prop-1-enyloxy methyl)oxirane and bisphenol A in a molar ratio of 8:1, the product of the reaction is

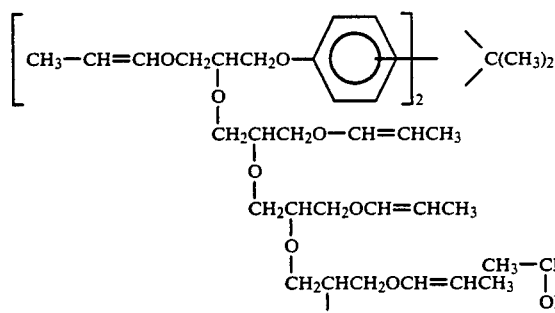

I.

usually in admixture with isomeric forms thereof, e.g. where the sum of $R_1$ substituents in the compound is equal to 8. Thus, some species may not be symmetrical and may have, for example two ring opened radicals substituted on the oxygen of one phenyl and six ring opened radicals substituted on the oxygen of the other phenyl radical.

When the same condensation reaction is carried out using a 4:1 molar ratio of the oxirane to bisphenol A, the corresponding product has the structure

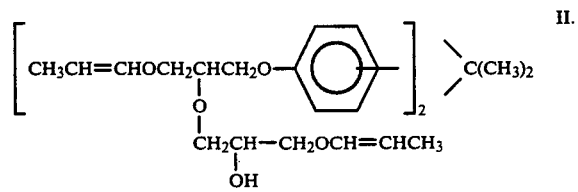

II.

usually in admixture with isomeric forms thereof as explained above.

It is to be understood that the products of this invention, in addition to their individual isomeric forms, can also be in the form of a cis and trans isomeric mixture wherein the ratio of cis to trans is dependent on the isomeric ratio in the alk-1-enyl oxirane reactant. More often the products of this invention are mixtures of cis and trans isomers.

A reaction mixture of alkenyloxy oxirane, alkyl epoxide and hydroxylated components results in the corresponding product mixture. Thus, the reaction of (prop-1-enyloxy methyl)oxirane, propylene oxide and dihydroxy benzene in a molar ratio of 2:1 (total oxides to diol), wherein the oxirane component contains about 50 mole % propylene oxide, results in a product mixture of

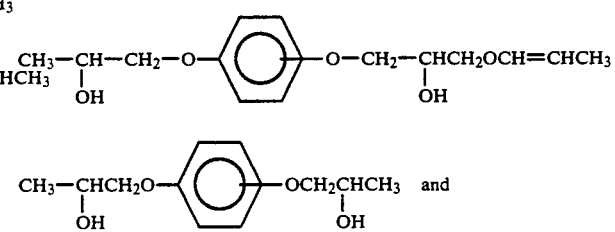

III.

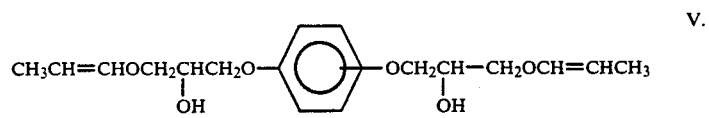

IV.

and

V.

It will be understood that when other polyols, such as tri and tetra hydroxylated reactants are involved, the same condensation reactions shown above can occur at the hydroxy sites of the hydroxylated reactant; thus leading to highly substituted products depending upon the particular polyol and the molar ratio of the respective reactants.

The following formula VI illustrates a reaction product of a phenol-formaldehyde condensation resin and (prop-1-enyloxy methyl) oxirane, where the molar ratio of oxirane per -OH group is 1:1.

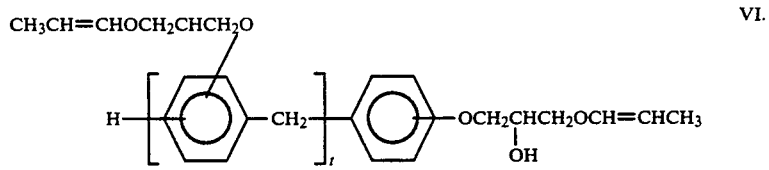

VI.

where t has a value of from 10 to 40.

The product obtained from (prop-1-enyloxy methyl), oxirane and pentaerythritol in molar proportion of 4:1 is

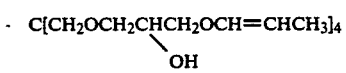

VII.

This product may also contain some mono-, di- and/or trisubstituted species, e.g.

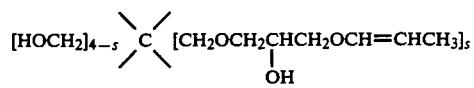

where s has a value of from 1 to 4.

As pointed out above, the hydroxy reactant can have a linear, branched, cyclic aliphatic or aromatic structure and can be monomeric or polymeric. Examples of suitable hydroxylated reactants include polyalkylene glycols, hydrogenated bisphenol A, halogenated bisphenol A, bisphenol A, alkoxylated bisphenol A, dihydroxyphenyl ether, resorcinol, hydroquinone, tetrahydrofuran dimethanol, petunidin chloride, methyl hydroxypentanol, pentaerythritol, trimethylol propane, trimethylol ethane, dihydroxyethylbenzoate, dihydroxy naphthyl hexanone, phenol, bisphenol, polyphenol, methanol, ethanol, propanol, butanol, octanol, ethylene glycol, propylene glycol, ethylene chlorohydrin, butanediol, phenaglycodol, butenediol, butynediol, glycerol, glyceryl, hydroxybutyl vinyl ether, monochlorohydrin, cresol, benzyl alcohol, hydroxy-methyl acetophenone, cresyl acetate, cyclohexanol, halogenated phenols, catechol, hexylresorcinol, trihydroxybenzene, a phenol-formaldehyde condensate resin, tetrahydroxybenzene, dihydroxy phenyl methane, trihydroxy butane, tetralol, naphthol, anthranol, etc. and natural alcohols such as cellulose, starches, and sugars and alkoxylated derivatives thereof.

The alk-1-enyloxy oxirane reactant contains from 4 to 28 carbon atoms, examples of which include 1-methyl-2-(prop-1-enyloxy) oxirane, (3-ethenyloxy propyl) oxirane, (4-ethenyloxy-butyloxy) methyl oxirane, 1-butyl-2-[2-(but-1-enyloxy) ethyl]oxirane, [4-(prop-1-enyloxy) butyl]oxirane, [2-(prop-1-enyloxy) ethyl]oxirane, 1-butyl-2[(but-1-enyloxy) ethyl]oxirane, [(prop-1-enyloxy) methyl]oxirane, [2-(vinyloxy) ethyl]oxirane, 1-ethyl-2-[(prop-1-enyloxy)methyl]oxirane, 1-methyl-1-ethyl-2-[3-(hex-1-enyloxy)propyl]oxirane, 1-methyl-2-[2-(but-1-enyloxy) ethyl]oxirane, 1-ethyl-2-[4-(vinyloxy)butyl]oxirane, (ethenyloxy methyl) oxirane, 1-propyl-2-[2-(prop-1-enyloxy) ethyl]oxirane, 1,1-dimethyl-2-[2-(but-1-enyloxy) ethyl]oxirane, 1-hexyl-2-[8-(prop-1-enyloxy) octyl]oxirane, etc.

Alkyl epoxides which may or may not be included in the reaction mixture are those having from 2 to 26 carbon atoms and include as representative examples, ethylene oxide, propylene oxide, dibutyl-ethylene oxide, tetramethyl-ethylene oxide, diethyl-ethylene oxide, triethyl-ethylene oxide, butylene oxide, butadiene monoxide, epichlorohydrin, epibromohydrin, epifluorohydrin, vinyl cyclohexane epoxide, hexyl-ethylene oxide, etc.

The mole ratio of hydroxylated compound to total oxide reactant can vary between about 1:1 and about 1:300, depending upon the number of -OH groups in the hydroxylated compound and the stoichiometric ratio of total oxide/-OH and the degree of -H substitution desired. More desirably, when the hydroxylated compound is a diol, a mole ratio of between about 1:2 and 1:16 diol to oxide is employed. When the hydroxylated compound is an polyhydroxy alkane containing up to 4 hydroxy groups, e.g. pentaerythritol, tetrahydroxy butane, etc. the mole ratio of hydroxylated alkane to total oxide is between about 1:4 and 1:64. The mole ratio of the alk-1-enyl oxirane to alkyl epoxide can vary between about 1:0 and about 1:20.

The reaction is carried out in the presence of a base catalyst such as, e.g. sodium or potassium metal, sodium or potassium methoxylate, hydroxide, alkoxide, hydride, phenoxide, or an alkaline earth metal hydroxide or alkoxide. Also, alkali or alkaline earth metal salts of reactant A can be employed. The catalyst is employed in a concentration of between about 0.1 and about 5 wt. %, preferably between about 0.4 and about 1 wt. %, based on total reactants.

In cases where the mixture of reactants provides a liquid having a viscosity such that good agitation becomes difficult, up to about 90 wt. % of an inert solvent can be added to the mixture. Suitable solvents include toluene, xylene, benzene; ethers such as alkyl ethers, e.g. methyl ethyl ether, diethyl ether, dibutyl ether, 1,2-dimethoxyethane, bis(2-methoxyethyl) ether, tetrahydrofuran; ketones such as methyl ethyl ketone; amides such as N-methyl-pyrrolidone, dimethyl formamide, N-ethyl-pyrrolidone;esters such as butyrolactone and ethyl acetate; nitriles such as acetonitrile and benzonitrile, cyclic carbonates such as ethylene and propylene carbonates and the like which have a boiling point below that of the reaction product.

The present reaction is effected in the liquid phase by agitating the reactants under a blanket of inert gas, e.g. nitrogen, argon, etc., at a temperature within the range of between about 50° and about 150° C. under from about atmospheric pressure up to about 1,000 psi when volatile reactants are employed in the reaction mixture. The reaction takes place over a period of from about 1 to 48 hours. Preferred reaction conditions include a temperature of between about 90° and about 135° C. under a pressure not exceeding 200 psi for a period of from about 2 to 20 hours.

When the reaction product mixture is highly viscous, any of the above named solvents can be added for dilution and the crude reaction mixture treated to remove catalyst. For example water can be added to the mixture to form a 2-phase liquid and to take up catalyst in the aqueous phase. The organic phase containing product is separated from the aqueous phase and dried to remove water and any solvent which may have been added to lower viscosity is removed under reduced pressure. Alternatively, a weakly acid ion exchange resin, e.g. Amberlite, IRC-50 or an inorganic adsorbent such as Magnesol, can be added to the reaction mixture to precipitate the catalyst whereupon the desired product is recovered by filtration.

The products of this process are useful as molding resins, adhesives and as highly solvent resistant coating materials which undergo substantially instantaneous curing thermally or curing by irradiation to provide clear, colorless, flexible films when applied to a substrate.

Having thus generally described the invention, reference is now had to the accompanying examples which illustrate preferred embodiments but which are not to be construed as limiting to the scope of the invention as more broadly set forth above and in the accompanying examples.

EXAMPLE I

In a 500 ml 3-necked round bottomed glass flask equipped with a mechanical stirrer, a thermometer, a water condenser and a nitrogen inlet was mixed 57 g. of bisphenol A, 230 g. of 74%-26% cis/trans [(prop-1-enyloxy)methyl]oxirane (mole ratio of 1:8). To this mixture, 2.5 g. of NaOCH$_3$ was added and the resulting mixture agitated under a blanket of nitrogen. After 12 hours at 130° C. under ambient pressure proton NMR indicated completion of the reaction and 250 cc of toluene was then added. The reaction product was recovered by washing with three 250 g. portions of H$_2$O, thus forming an aqueous phase and an organic phase. The organic layer containing product was separated, dried with magnesium sulfate, filtered and toluene was evaporated under reduced pressure. A clear yellow liquid, 225 g., of the product having the formula

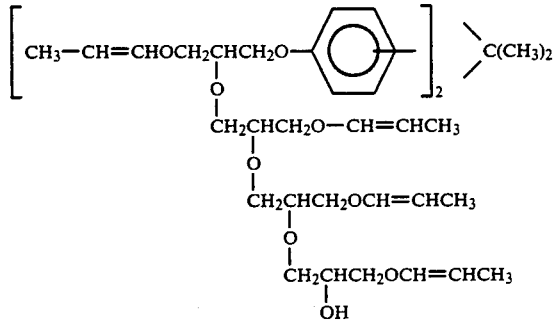

was recovered in admixture with isomeric species thereof.

The above reaction was repeated except that 54%–46% cis/trans [(prop-1-enyloxy)methyl]oxirane was substituted. The substitution of this reactant had no material affect and the product was identical to that described above except for the cis/trans product distribution.

EXAMPLE II

Example I is repeated except that 114 g. of the oxirane reactant (54%–46% cis/trans) was employed to provide a mole ratio of 1:4. The resulting product

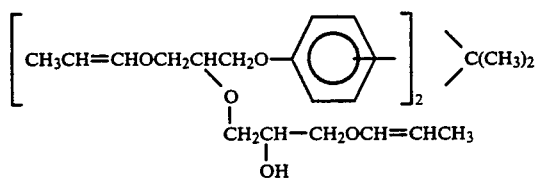

was obtained in 94% yield.

EXAMPLE III

Example I is repeated except that 57 g. of the oxirane reactant was employed to provide a 1:2 mole ratio and resorcinol is substituted for bisphenol A. The product having the formula

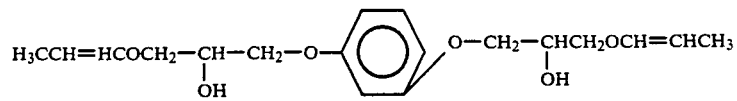

is recovered in 95% yield.

EXAMPLE IV

A 500 ml 3-necked round bottomed flask equipped with a mechanical stirrer, thermometer, water condenser and nitrogen inlet was charged with 114 g. (0.5 mole) of bisphenol A, 120 g. (1.05 moles) of [(prop-1-enyloxy)methyl]oxirane (74%–26% cis/trans), i.e. mole ratio of 1:2, and 2.5 g. of sodium methoxide. The flask was heated to 130° C. and stirred for 5 hours under nitrogen. Progress of the reaction was monitored by withdrawing samples of the reaction mixture every hour via proton NMR. The product mixture was then diluted with 250 ml of toluene.

The product was recovered by washing with three 250 g. portions of water. The resulting organic layer was separated from the aqueous layer and dried with magnesium sulfate, filtered, and the toluene removed under reduced pressure. The final product (200 g.) was a clear yellow viscous liquid having the formula

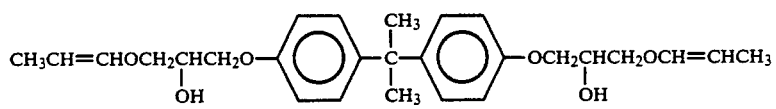

as indicated by proton NMR and infrared spectra.

EXAMPLE V

In a reactor similar to the one described in Example IV. Bisphenol A (114 g.), 250 g. of [(prop-1-enyloxy)-methyl]oxirane (74%–26% cis/trans) i.e. a mole ratio of 1:4 and 5 g. of sodium methoxide were stirred at 130° C. under a blanket of nitrogen. After 5 hours the reaction was complete as indicated by proton NMR spectroscopy. The product, 320 g., of a yellow oily liquid having the formula

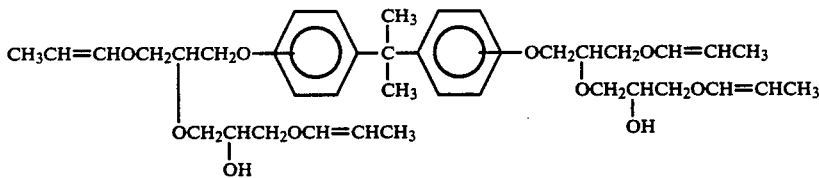

as indicated by proton NMR spectrum was recovered in admixture with a minor amount of isomers thereof.

Other examples employing different cis/trans ratios, e.g. 54%–46%, were employed but found to have no material effect on the reaction or product obtained.

EXAMPLE VI

In a 3-liter reactor similar to that described in Example IV, 570 g. bisphenol A, 1,140 g. [(prop-1-enyloxy)-methyl]oxirane (60%–40% cis/trans), and 5.0 g. sodium methoxide were combined. This mixture was stirred at 120° C. under nitrogen gas. After 7 hours, proton NMR indicated complete conversion of the oxirane.

The product was isolated by diluting the crude reaction mixture with an equal volume of tetrahydrofuran. To this stirred solution was added 15 g. of Amberlite®IRC-50 ion exchange resin. After 2 hours, the Amberlite resin was filtered away and 100 g. of Magnesol was slurried with the filtrate for 2 hours followed by filtration. Tetrahydrofuran was then removed under reduced pressure and 1362 g. of the clear, yellow, organic liquid product described in Example II was obtained.

EXAMPLE VII

To a glass reactor equipped with a mechanical stirrer, thermometer, condenser, and nitrogen inlet 114 g. of [(prop-1-enyloxy)methyl]oxirane, 57 g. of hydrogenated bisphenol A and 0.5 g. of sodium methoxide were charged. This mixture was stirred and maintained at 130° C. for 16 hours. To remove the base catalyst the crude product was diluted with 150 cc of tetrahydrofuran and slurried vigorously with 5 g. of Magnesol for one hour. The Magnesol was then filtered off and the tetrahydrofuran removed under reduced pressure. The remaining product was a yellow viscous liquid which slowly solidified upon standing after several days. This product had the structure $$[CH_3CH=CHOCH_2CHCH_2O\underset{|}{-}\!\!\langle\!\!\bigcirc\!\!\rangle\!\!-]_2 \!\!>\!\!C(CH_3)_2$$
$$\underset{OH}{\overset{|}{O}CH_2CHCH_2OCH=CHCH_3}$$

which was obtained with isomers thereof.

EXAMPLE VIII

To a glass reactor equipped with a thermometer, mechanical stirrer, condenser and nitrogen inlet 114 g. of [(prop-1-enyloxy)methyl]oxirane, 34 g. of pentaerythritol, and 0.5 g. sodium methoxide were charged. This mixture was stirred and heated to 115° C. under nitrogen for 5 hours. The catalyst was removed as in Example VII by treatment with Magnesol, after which a clear yellow liquid product having the formula $$C[CH_2OCH_2\underset{\underset{OH}{|}}{C}HCH_2OCH=CHCH_3]_4$$

was obtained in mixture with less than 5% of the corresponding mono-, di- and tri- substituted products.

EXAMPLE IX

Example II is repeated except that 344 g. of [4-(ethenyloxy)butyloxy methyl]oxirane is substituted for [(prop-1-enyloxy)methyl]oxirane. Using the 1:4 molar ratio, the resulting product $$[CH_2\!\!=\!\!CHOC_4H_8OCH_2CHCH_2O\!\!-\!\!\langle\!\!\bigcirc\!\!\rangle\!\!-]_2 \!\!>\!\!C(CH_3)_2$$
$$\underset{OH}{\overset{|}{O}CH_2CHCH_2OC_4H_8OCH=CH_2}$$

in isomeric mixture is obtained in 90% yield.

EXAMPLE X

Example II is repeated except that [(ethenyloxy)methyl]oxirane is substituted for [(prop-1-enyloxy)methyl]oxirane. The product having the formula:

$$\left[CH_2\!\!=\!\!CHOCH_2CHCH_2O\!\!-\!\!\langle\!\!\bigcirc\!\!\rangle\!\!-\right]_2 \!\!>\!\!C(CH_3)_2$$
$$\underset{OH}{\overset{|}{O}CH_2CH\!-\!CH_2OCH=CH_2}$$

in isomeric mixture is recovered in 95% yield.

EXAMPLE XI

In a one liter reactor equipped with a mechanical stirrer, a thermometer, a dry ice condenser and a nitrogen inlet was mixed 114 g. of bisphenol A in 300 cc of 2-methoxy ethyl ether. To this mixture, 57 g. of [(prop-1-enyloxy)methyl]oxirane and 29 g. of propylene oxide was slowly added and the resulting mixture agitated for 5 hours at 120° C. under atmospheric pressure. The reaction product was recovered by washing with three 250 g. portions of H₂O, thus forming an aqueous phase and an organic phase. The organic layer containing product was separated, dried with magnesium sulfate, filtered and solvent was evaporated under reduced pressure. A clear yellow liquid product mixture of the following components was obtained.

$$CH_3\!\!-\!\!\underset{\underset{OH}{|}}{C}H\!\!-\!\!CH_2\!\!-\!\!O\!\!-\!\!\langle\!\!\bigcirc\!\!\rangle\!\!-\!\!\underset{\underset{CH_3}{|}}{\overset{CH_3}{\overset{|}{C}}}\!\!-\!\!\langle\!\!\bigcirc\!\!\rangle\!\!-\!\!O\!\!-\!\!CH_2\!\!-\!\!\underset{\underset{OH}{|}}{C}HCH_2OCH=CHCH_3$$

$$CH_3\!\!-\!\!\underset{\underset{OH}{|}}{C}HCH_2O\!\!-\!\!\langle\!\!\bigcirc\!\!\rangle\!\!-\!\!\underset{\underset{CH_3}{|}}{\overset{CH_3}{\overset{|}{C}}}\!\!-\!\!\langle\!\!\bigcirc\!\!\rangle\!\!-\!\!OCH_2\underset{\underset{OH}{|}}{C}HCH_3 \quad\text{and}$$

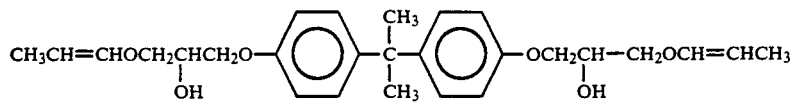

EXAMPLE XII

In a 1 liter glass reactor equipped with a mechanical stirrer, thermometer, condenser, and nitrogen inlet was added 127 g. of phenol, 342 g. of [(prop-1-enyloxy)methyl]oxirane and 25 g. of sodium methoxide. This mixture was stirred at room temperature under a blanket of nitrogen for 7 hours. Exothermic conditions caused the temperature of the reaction mixture rise to 150° C. After 3 hours the reaction cooled to about room temperature whereupon the product was recovered in 90% yield by flash distillation under reduced pressure. Proton NMR spectroscopy showed the product to have the structure:

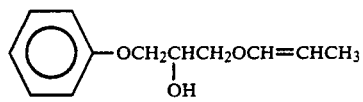

EXAMPLE XIII

In a 500 cc glass reactor equipped with a mechanical stirrer, condenser, nitrogen inlet, and thermometer is added 114 g. of bisphenol A, 57 g. of [(prop-1-enyloxy)-methyl]oxirane and 200 g. cc of 2-methoxyethyl ether. This mixture is stirred at 120° C. for 6 hours under nitrogen gas. The product having the formula

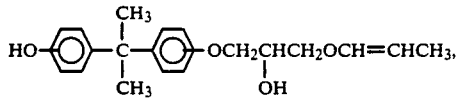

including a minor amount of the disubstituted product, is recovered using the procedure of Example VI.

EXAMPLE XIV

In a glass reactor equipped as described in Example XIII, 100 g. of methanol, 145 g. of (prop-1-enyloxymethyl)oxirane and 0.25 g. of sodium methoxide was combined. This mixture was stirred at 50° C. for 2 hours under a blanket of nitrogen. The reaction was cooled, the excess methanol removed by rotary evaporation and the product recovered in greater than 90% yield by simple flash distillation. The proton NMR spectrum identified the product as having the formula:

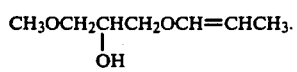

It will be understood that many modifications and substitutions can be made in the above examples to provide the novel compounds of this invention. For example, other oxiranes, such as [(but-1-enyloxy)butyl]oxirane, [(pent-1-enyloxy)butenyl]oxirane, [(prop-i-enyloxy)methyl]dimethyl oxirane and the like as well as other alkylene epoxides, such as dibutyl-ethyl epoxide, epichlorohydrin, tetramethyl ethyl epoxide, butenyl ethyl epoxide and the like can be substituted in any of the foregoing examples. Also, other hydroxylated compounds can be substituted therein. For example monohydroxylated and polyhydroxylated alkanes of 2 or more carbon atoms, a starch or a sugar, an polyethoxylated or polypropoxylated butanediol, dichlorobutanediol, and the like are representative. All of the above are included in the scope of this invention.

What is claimed is:

1. The process which comprises conacting a hydroxylated compound having the formula

and from about 1 to about 64 moles/mole of HO of an alk-1-enyloxy oxirane having the formula

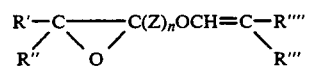

which oxirane contains from 0 to 95 wt. % of alkyl epoxide having the formula

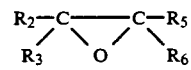

wherein m has a value of from 0.to 8; t has a value of from to 5? ; when m is a positive integer, R is $C_2$ to $C_{20}$ alkylene, alkenylene, alkynylene, arylene, aralkylene, alkarylene, aralkenylene or alkenylarylene which radicals are optionally substituted with a carbonyl, vinyl ether, carboxylate, carbonate, alkyloxyalkyl, alkenyloxyalkyl, halo, hydroxy, alkyloxy or a mixture thereof and when m is zero, R can be $C_1$ to $C_{20}$ alkyl, phenyl, benzyl, a polyhydroxylated starch, cellulose or sugar and alkoxylated derivatives thereof; or the radical

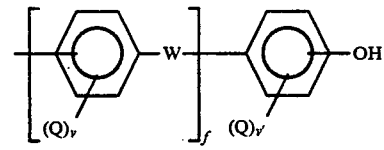

where

W is lower alkyl, sulfur, sulfonyl or oxygen; Q and Q' are each independently lower alkyl or halogen; v and v' each have a value of from 0 to 4 and f has a value of from 1 to 50;

Z is $C_1$ to $C_8$ alkylene, alkenylene, alkynylene or alkoxy;

R', R'', R''' and R'''' are each independently hydrogen or alkyl having from 1 to 6 carbon atoms;

n has a value of from 1 to 8; and $R_2$, $R_3$, $R_5$ and $R_6$ are each independently hydrogen, $C_1$ to $C_6$ alkyl or alkenyl or halogenated alkyl or alkenyl; reacting the above named components in the presence of a base catalyst at a temperature of between about 50° C. and about 150° C. under from about 14 to about 1,000 psi for a period of from about 1 to about 48 hours.

2. The process of claim 1 wherein said components are reacted at a temperature of between about 90° C. and about 135° C. under a pressure up to 200 psi for a period of from about 2 to about 10 hours.

3. The process of claim 1 wherein said oxirane is a viscous material and is dissolved in an inert solvent prior to reaction with said hydroxylated compound.

4. The process of claim 1 wherein said base catalyst is sodium or potassium methoxylate.

5. The process of claim 1 wherein said hydroxylated compound is bisphenol A.

6. The process of claim 1 wherein said hydroxylated compound is pentaerythritol.

7. The process of claim 5 wherein said alk-1-enyloxy oxirane is 1-[(prop-1-enyloxy)methyl oxirane.

8. The product of the process of claim 1.

9. The composition comprising the hydroxylated compound and the alk-1-enyloxy oxirane containing from 0 to 95% of the alkyl epoxide of claim 8 in a molar ratio of —OH in said hydroxylated compound to total oxides of between 1:1 and about 1:64.

10. The composition of claim 9 wherein the hydroxylated compound is a diol and the ratio of diol to total oxides is between 1:2 and 1:16.

* * * * *